United States Patent [19]

Moyer

[11] Patent Number: 5,646,025

[45] Date of Patent: Jul. 8, 1997

[54] SCYTALIDIUM CATALASE GENE

[75] Inventor: Donna Moyer, Davis, Calif.

[73] Assignee: Novo Nordisk A/S, Bagsvaerd, Denmark

[21] Appl. No.: 435,925

[22] Filed: May 5, 1995

[51] Int. Cl.$^6$ .............................. C12N 9/08; C12N 15/53; C12N 15/63; C12N 15/80

[52] U.S. Cl. .................... 435/192; 435/69.1; 435/172.3; 435/252.3; 435/320.1; 536/23.2; 935/14; 935/23; 935/28; 935/68

[58] Field of Search ........................ 435/192, 69.1, 435/172.3, 252.3, 254.2, 254.3, 320.1; 536/23.2

[56] References Cited

U.S. PATENT DOCUMENTS 4,652,639  3/1987  Stabinsky ..................... 435/91.52

FOREIGN PATENT DOCUMENTS

WO92/17571  10/1992  WIPO.
WO93/17721  9/1993  WIPO.
WO93/18166  9/1993  WIPO.

OTHER PUBLICATIONS

JP 5153975 (abstract only).
JP 63017693 (abstract only).
JP 1086879 (abstract only).
JP 3103182 (abstract only).
Vainshtein et al., J. Mol. Biol. 188: 63–72, 1986 (abstract only).
Jacob and Orme–Johnson, Biochemistry 18:2967–2975, 1979 (abstract only).
Jacob and Orme–Johnson, Biochemistry 18: 2975–2980, 1979 (abstract only).
Fortkamp, E., et al., DNA, vol. 5, "Cloning and expression in Escherichia coli of a synthetic DNA for hirudin, the blood coagulation inhibitor in the leech", pp. 511–517 1986.
Furuta, S., et al., Proceedings of the National Academy of Sciences, U.S.A., vol. 83, "Complete nucleotide sequence of cDNA and deduced amino acid sequence of Drosophila catalase", p. 3663 (1990).
Orr, E. C., et al., Nucleic Acids Research, vol. 18, "cDNA and deduced amino acid sequence of Drosophila catalase", p. 3663 1990.
Ossowski, I., et al., Journal of Bacteriology, vol. 173, "Nucleotide sequence of Eschericha coli katE, which encodes catalase HPII", 514–520 1991.
Fowler, T., et al., Molecular Microbiology, vol. 9, "The catR gene encoding a catalase from Aspergillus niger: primary structure and elevated expression through increased gene copy number and use of a strong promoter", pp. 989–998 1993.

*Primary Examiner*—Robert A. Wax
*Assistant Examiner*—William W. Moore
*Attorney, Agent, or Firm*—Steve T. Zelson, Esq.; Elias J. Lambiris, Esq.

[57] ABSTRACT

The present invention relates to a nucleic acid construct containing a nucleic acid sequence encoding a Scytalidium catalase enzyme, as well as vectors and host cells comprising the construct.

21 Claims, 11 Drawing Sheets

PmeST5 (forward primer)

5'                                    3'
agcactagtttaaacTAYGARGTIGAYGA
              Y   E   V   D   D     peptide sequence(AA 45-49)

St3.2not (reverse primer)

5'                                    3'
tattggatataagcggccgCCCYTGICGYTTYTTGAARTG
                   G  Q  R  K  K  F  H   (AA 271-265)

```
      9           18          27          36          45          54
>
ATG AAC AGA GTC ACG AAT CTC CTC GCC TGG GCC GGC GCG ATA GGG CTC GCC CAA
 M   N   R   V   T   N   L   L   A   W   A   G   A   I   G   L   A   Q 63          72          81          90          99         108
GCA ACA TGT CCC TTT GCG GAC CCT GCC GCT CTG TAT AGT CGT CAA GAT ACT ACC
 A   T   C   P   F   A   D   P   A   A   L   Y   S   R   Q   D   T   T 117         126         135         144         153         162
AGC GGC CAG TCG CCA CTT GCA GCA TAC GAG GTG GAT GAC AGC ACC GGA TAC CTG
 S   G   Q   S   P   L   A   A   Y   E   V   D   D   S   T   G   Y   L 171         180         189         198         207         216
ACC TCC GAT GTT GGC GGG CCC ATT CAG GAC CAG ACC AGC CTC AAG GCA GGC ATC
 T   S   D   V   G   G   P   I   Q   D   Q   T   S   L   K   A   G   I 225         234         243         252         261         270
CGG GGT CCG ACC CTT CTT GAG GAC TTT ATG TTC CGC CAG AAG ATC CAG CAC TTC
 R   G   P   T   L   L   E   D   F   M   F   R   Q   K   I   Q   H   F 279         292         302         312         322         332
GAC CAT GAA CGG GTAAGGACAT AATGCTCACA CGAGCGGCTG CGTGCCCACC TATTTCCGAG
 D   H   E   R 342         352         362         372         382         392        402
ACATTGGGCT GGCTGGCTGG CTGTGACTGC TTGAGTTTGG GGACATACGG AGTACCTTAC TGACGCGCTG 412         422         431         440         449
AACCACTCCA G GTT CCC GAA AGG GCG GTC CAT GCT CGA GGC GCT GGA GCA CAC
             V   P   E   R   A   V   H   A   R   G   A   G   A   H 458         467         476         485         494         503
GGG ACC TTC ACG AGT TAC GCC GAC TGG AGT AAC ATC ACC GCG GCG TCC TTT CTG
 G   T   F   T   S   Y   A   D   W   S   N   I   T   A   A   S   F   L 512         521         530         539         548         557
AAC GCC ACT GGA AAG CAG ACG CCG GTG TTT GTC CGG TTC TCG ACC GTT GCT GGG
 N   A   T   G   K   Q   T   P   V   F   V   R   F   S   T   V   A   G 566         575         584         593         602         611
TCT CGA GGG AGC GCA GAC ACG GCG AGA GAC GTT CAT GGT TTC GCG ACG CGG TT
 S   R   G   S   A   D   T   A   R   D   V   H   G   F   A   T   R   F
```

FIG. 4B

```
       626        636        646        656         666        676       686
GTAAGTTTTG TTGTGTTTCA TTCGTTCCGG TCTGTAGAGG AGGGTTAGGA TATGAGCTAA CGTGTGTGTG 695             705        714                 728        738      748
TGTGTGAAG T TAC ACT GAT GAA GGC AAC TTT G GTACGTCCCA CGCATGGTCC TCAATTCTCT
            Y   T   D   E   G   N   F   D 758        768        778        788         799        808
TATCTGGCAG CCATGTGGTC ATTGTCGACG TTGCTAACTT GCGTAG AT ATC GTC GGA AAC
                                                     I   V   G   N 817        826        835        844         853        862
AAC ATC CCG GTA TTC TTC ATT CAA GAT GCA ATC CAG TTC CCT GAC CTT ATC CAC
 N   I   P   V   F   F   I   Q   D   A   I   Q   F   P   D   L   I   H 871        880        889        898         907        916
TCG GTC AAG CCG CGT CCC GAC AAC GAG ATT CCC CAA GCG GCG ACG GCT CAT GAT
 S   V   K   P   R   P   D   N   E   I   P   Q   A   A   T   A   H   D 925        934        943        952         965        975
TCA GCT TGG GAC TTC TTC AGC CAG CAG CCA AGC ACC ATG GTAAGCAATG GACCAAGGAG
 S   A   W   D   F   F   S   Q   Q   P   S   T   M 985        995       1005       1015        1025       1035      1045
CCGCACCTGG GGTGACATGC CAGGGAGTAC ACAAGGCGTT CCGATGACCC TCGTGTGACC AAGGCAGTAC 1055       1065       1075       1085        1095       1105
AACACTCCAC GGAGGACTCG AAGAGATTCG GCAATATGGA ACACAGAACT GACAGGATGG TAG 1114       1123       1132       1141        1150       1159
CAC ACG TTG TTC TGG GCC ATG TCC GGC CAC GGA ATC CCT CGC AGC TAC CGC CAT
 H   T   L   F   W   A   M   S   G   H   G   I   P   R   S   Y   R   H 1175       1185       1195        1205       1215       1224
ATG GTACGTTTGC CTGGCTGAGA TGACCGTGAA TCCATTTCTA ACCTCAAGCC CAG GAT GGC
 M                                                          D   G 1233       1242       1251       1260        1269       1278
TTC GGC GTC CAC ACG TTC CGG TTT GTC AAA GAT GAC GGC TCG TCC AAG TTG ATC
 F   G   V   H   T   F   R   F   V   K   D   D   G   S   S   K   L   I 1287       1296       1305       1314        1323       1332
AAG TGG CAT TTC AAG TCA CGC CAG GGA AAG GCG AGT CTA GTC TGG GAA GAG GCG
 K   W   H   F   K   S   R   Q   G   K   A   S   L   V   W   E   E   A
```

```
      1341           1350           1359           1368           1377
                                                                           1386
CAG  GTT  CTT  TCT  GGC  AAG  AAT  GCC  GAC  TTC  CAC  CGT  CAG  GAC  CTC  TGG  GAT  GCT
 Q    V    L    S    G    K    N    A    D    F    H    R    Q    D    L    W    D    A 1395           1404           1413           1422           1431
                                                                           1440
ATT  GAG  TCC  GGG  AAC  GGA  CCA  GAA  TGG  GAT  GTC  TGC  GTC  CAG  ATT  GTC  GAT  GAG
 I    E    S    G    N    G    P    E    W    D    V    C    V    Q    I    V    D    E 1449           1458           1467           1476           1485
                                                                           1494
TCC  CAG  GCG  CAA  GCC  TTT  GGC  TTC  GAC  TTG  CTG  GAC  CCG  ACA  AAG  ATC  ATC  CCC
 S    Q    A    Q    A    F    G    F    D    L    L    D    P    T    K    I    I    P 1503           1512           1521           1530           1539
                                                                           1548
GAG  GAG  TAC  GCC  CCC  TTG  ACG  AAG  CTG  GGC  CTC  TTG  AAG  CTG  GAT  CGC  AAT  CCG
 E    E    Y    A    P    L    T    K    L    G    L    L    K    L    D    R    N    P 1557           1566           1575           1584           1593
                                                                           1602
ACC  AAC  TAC  TTC  GCC  GAG  ACG  GAG  CAG  GTC  ATG  TTC  CAA  CCC  GGT  CAT  ATC  GTC
 T    N    Y    F    A    E    T    E    Q    V    M    F    Q    P    G    H    I    V 1611           1620           1629           1638           1647
                                                                           1656
CGC  GGC  ATC  GAC  TTC  ACG  GAG  GAT  CCC  CTG  CTA  CAG  GGA  CGC  CTC  TTT  TCG  TAC
 R    G    I    D    F    T    E    D    P    L    L    Q    G    R    L    F    S    Y 1665           1674           1683           1692           1701
                                                                           1710
CTT  GAC  ACG  CAG  CTG  AAC  CGG  AAT  GGC  GGG  CCC  AAC  TTT  GAG  CAG  CTG  CCC  ATC
 L    D    T    Q    L    N    R    N    G    G    P    N    F    E    Q    L    P    I 1719           1728           1737           1746           1755
                                                                           1764
AAC  ATG  CCG  CGG  GTG  CCG  ATT  CAC  AAC  AAT  AAT  CGC  GAC  GGC  GCC  GGC  CAG  ATG
 N    M    P    R    V    P    I    H    N    N    N    R    D    G    A    G    Q    M 1773           1782                         1799           1809
                                                                           1819
TTC  ATC  CAC  AGG  AAC  AAG  TAT  CCT  T    GTAAGTGCCT  CTTTTGCCTC  GATCGTTGTG
 F    I    H    R    N    K    Y    P    Y 1829           1839           1848           1857           1866
                                                                           1875
GTGCCGGCTT  GCTGACAGAC  GCAG  AC  ACT  CCC  AAC  ACC  CTG  AAC  AGT  GGT  TAT  CCG
                              T    P    N    T    L    N    S    G    Y    P 1884           1893           1902           1911           1920
                                                                           1929
CGG  CAA  GCC  AAC  CAA  AAT  GCC  GGA  CGC  GGA  TTC  TTC  ACA  GCG  CCT  GGC  CGT  ACC
 R    Q    A    N    Q    N    A    G    R    G    F    F    T    A    P    G    R    T 1938           1947           1956           1965           1974
                                                                           1983
GCC  AGC  GGT  GCC  CTC  GTC  CGT  GAG  GTG  TCG  CCA  ACA  TTC  AAC  GAC  CAC  TGG  TCG
 A    S    G    A    L    V    R    E    V    S    P    T    F    N    D    H    W    S
```

*FIG.4C*

```
     1992         2001         2010         2019         2028          2037
 CAG  CCC  CGT  CTC  TTC  TTC  AAC  TCC  CTC  ACT  CCC  GTC  GAA  CAA  CAG  TTC  CTC  GTC
  Q    P    R    L    F    F    N    S    L    T    P    V    E    Q    Q    F    L    V 2046         2055         2064         2073         2082          2091
 AAC  GCC  ATG  CGC  TTC  GAA  ATC  AGC  CTT  GTG  AAG  TCG  GAA  GAA  GTC  AAG  AAG  AAC
  N    A    M    R    F    E    I    S    L    V    K    S    E    E    V    K    K    N 2100         2109         2118         2127         2136          2145
 GTG  CTC  ACC  CAG  CTC  AAC  CGC  GTC  AGC  CAT  GAC  GTG  GCC  GTG  CGC  GTG  GCC  GCC
  V    L    T    Q    L    N    R    V    S    H    D    V    A    V    R    V    A    A 2154         2163         2172         2181         2190          2199
 GCT  ATC  GGC  CTC  GGC  GCG  CCC  GAC  GCG  GAC  GAC  ACA  TAC  TAC  CAC  AAC  AAC  AAG
  A    I    G    L    G    A    P    D    A    D    D    T    Y    Y    H    N    N    K 2208         2217         2226         2235         2244          2253
 ACG  GCT  GGC  GTC  TCA  ATC  GTT  GGA  AGC  GGG  CCC  TTG  CCT  ACC  ATC  AAG  ACT  CTC
  T    A    G    V    S    I    V    G    S    G    P    L    P    T    I    K    T    L 2262         2271         2280         2289         2298          2307
 CGC  GTC  GGC  ATC  CTG  GCT  ACC  ACG  AGC  GAG  TCG  AGC  GCG  CTG  GAT  CAG  GCG  GCC
  R    V    G    I    L    A    T    T    S    E    S    S    A    L    D    Q    A    A 2316         2325         2334         2343         2352          2361
 CAG  CTC  CGC  ACC  CGT  CTG  GAA  AAG  GAC  GGG  CTT  GTG  GTC  ACG  GTT  GTG  GCT  GAA
  Q    L    R    T    R    L    E    K    D    G    L    V    V    T    V    V    A    E 2370         2379         2388         2397         2406          2415
 ACG  CTG  CGC  GAG  GGG  GTA  GAC  CAG  ACG  TAC  TCG  ACG  GCG  GAT  GCC  ACG  GGT  TTC
  T    L    R    E    G    V    D    Q    T    Y    S    T    A    D    A    T    G    F 2424         2433         2442         2451         2460          2469
 GAC  GGC  GTT  GTT  GTT  GTG  GAC  GGG  GCG  GCG  GCG  CTG  TTT  GCC  AGC  ACC  GCG  TCG
  D    G    V    V    V    V    D    G    A    A    A    L    F    A    S    T    A    S 2478         2487         2496         2505         2514          2523
 TCG  CCG  TTG  TTC  CCG  ACG  GGC  AGG  CCG  TTG  CAG  ATC  TTT  GTG  GAC  GCG  TAT  CGG
  S    P    L    F    P    T    G    R    P    L    Q    I    F    V    D    A    Y    R 2532         2541         2550         2559         2568          2577
 TGG  GGA  AAG  CCG  GTC  GGT  GTG  TGT  GGT  GGG  AAG  TCG  AGC  GAG  GTG  TTG  GAT  GCG
  W    G    K    P    V    G    V    C    G    G    K    S    S    E    V    L    D    A 2586         2595         2604         2613         2622          2631
 GCG  GAT  GTT  CCG  GAA  GAC  GGG  GAC  GGG  GTG  TAT  TCG  GAG  GAG  TCG  GTG  GAC  ATG
  A    D    V    P    E    D    G    D    G    V    Y    S    E    E    S    V    D    M
```

*FIG. 4D*

```
          2640        2649        2658        2667         2680        2690
TTT GTG GAG GAG TTT GAG AAG GGG TTG GCT ACT TTC AGG GTGAGTCTTG ATGCCTTTGT
 F   V   E   E   F   E   K   G   L   A   T   F   R 2700        2710        2720        2730         2740        2750        2760
TTGTTGTGAT GTTATTGTTT TGTTTTGTCT CGGACTTTGT GAAAGAATGA CGGACTGACG TCTTTGGTAT 2770        2779        2788    2794
CTAG TTT ACC GAT CGG TTT GCT CTC GAC TCT TAG
      F   T   D   R   F   A   L   D   S
```

*FIG.4E*

```
     X             X
SGQSPLAAYEVDDSDGY        peptide STS2 [N-terminal sequence]
|||||||||||||| ||
SGQSPLAAYEVDDSTGY        from DNA sequence
X 40       50 X X     X
ADWS-ITAA                peptide Std1
|||| ||||
ADWSNITAA                from DNA sequence
X  120  X X      X
RNPTNYFAE                peptide STd2
|||||||||
RNPTNYFAE                from DNA sequence
350       X X              X
AYRWGKPVGVXGGKRRE        peptide STd3
|||||||||| ||| |
AYRWGKPVGVCGGKSSE        from DNA sequence
 660         670 X X         X
SFALDQAAQLR              peptide STd5
| |||||||||
SSALDQAAQLR              from DNA sequence
580       590

X      X
RFEISLVK                 peptide STS1A
||||||||
RFEISLVK                 from DNA sequence
X 505 X X      X
NVLTQLNRV                peptide STS1B
|||||||||
NVLTQLNRV                from DNA sequence
X 520 X X                                X
MDGFGVHTFRFVKDDGSSKLIKXHFKKRQGKA         peptide STS4
||||||||||||||||||||||| ||| |||||
MDGFGVHTFRFVKDDGSSKLIKWHFKSRQGKA         from DNA sequence
X      250       260       270 X
```

Figure 5

SCYTALIDIUM CATALASE GENE

FIELD OF THE INVENTION

The present invention relates to a nucleic acid construct comprising a nucleic acid sequence encoding a Scytalidium catalase gene.

BACKGROUND OF THE INVENTION

The enzyme known as catalase (EC 1.11.1.6) catalyzes the decomposition of hydrogen peroxide into water and molecular oxygen. In the cell, hydrogen peroxide is produced as a by-product of aerobic metabolism and has the potential to damage a variety of macromolecules including DNA (Brawn and Fridovich, Arch. Biochem. Biophys. 206: 414–419, 1981). Catalase is induced as a defense against $H_2O_2$-mediated damage.

The enzyme has been proposed for many commercial uses. In general terms, it can be used in any situation in which it is desired to remove residual hydrogen peroxide from a system to which hydrogen peroxide has been added, e.g., for pasteurization or bleaching. One such example is the use of catalase in the textile industry for the removal of hydrogen peroxide from fabric which is bleached by an alkaline hydrogen peroxide treatment before dyeing. A similar application is its use in pulp bleaching. Catalase can also be used in the removal of hydrogen peroxide from contact lenses after hydrogen peroxide disinfection.

A number of different types of catalases have been isolated and identified, from animal, plant and microbial sources. In particular a number of filamentous fungal catalases have been found. Those which have been characterized consist of four polypeptide subunits, each having a molecular weight of 80,000 to 97,000 and contain one heme prosthetic group per subunit. For example, catalase has been characterized from Penicillium (Vainshtein et al., J. Mol. Biol. 188: 63–72, 1986), from Neurospora (Jacob and Orme-Johnson, Biochemistry 18: 2967–2975, 1979), from Acremonium and Thermoascus (JP 5153975) and from Aspergillus (Fowler et al., Mol. Microbiol. 9: 989–998, 1993). The genes encoding certain of these catalases have also been isolated, and recombinant expression achieved (WO 93/17721, Wo 93/18166; JP 3103182; JP 1086879; JP 63017693); An extremely stable catalase, which retains activity at higher temperature and pH than other known catalases, has been isolated from strains of Scytalidium and Humicola (WO 92/17571). These properties make the Scytalidium/Humicola catalases particularly effective in the removal of residual peroxide in textile applications. However, recombinant production of this enzyme has not heretofore been accomplished. The present invention provides the gene encoding the Scytalidium catalase and a method for recombinant expression of same.

BRIEF DESCRIPTION OF THE FIGURES

FIG. 1 illustrates the PCR primers used to generate a 1.1 kb catalase probe. Upper case letters correspond to catalase sequence, and lower case letters correspond to restriction sites introduced by PCR (SEQ. ID NOS. 3 and 4)

FIG. 4 illustrates the S. thermophilum genomic clone nucleic acid and amino acid sequence (SEQ ID NOS.1 and 2)

FIG. 5 illustrates the homology of isolated catalase peptides to the translated DNA sequence.

SUMMARY OF THE INVENTION

Figure 2:
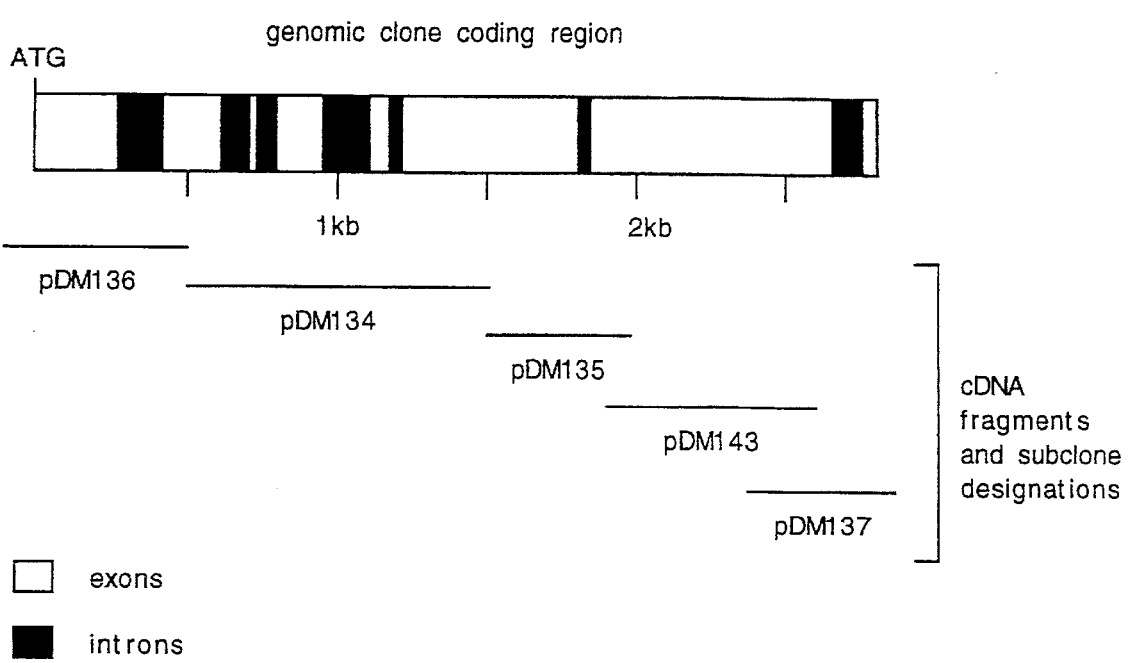
FIG. 2 illustrates the relative positions of the identified Scytalidium thermophilum cDNA subclones.

The present invention provides a nucleic acid construct comprising a nucleic acid sequence encoding a Scytalidium catalase. The invention also provides a method for production of a recombinant Scytalidium catalase which comprises culturing, for a time and under conditions conducive to expression of a catalase, a recombinant host cell containing a nucleic acid construct comprising a nucleic acid sequence encoding a Scytalidium catalase.

DETAILED DESCRIPTION OF THE INVENTION

The catalase produced by strains of the genus Scytalidium and the genus Humicola have been characterized in copending U.S. Ser. No. 08/117,201, the contents of which are incorporated herein by reference. Briefly, the enzyme is one which retains at least 75% residual activity after 20 minutes at 70° C., at pH 9–10.5. Organisms of the Humicola-Scytalidium complex are well known, and have been described by D. H. Ellis, Trans. Br. Mycol. Soc. 78(1): 129–139, 1982. All members of this complex have been assigned to two species: Humicola insolens(Cooney and Emerson) and Scytalidium thermophilum(Cooney and Emerson)Austwick. The definition and taxonomy of the genus Scytalidium is described by Pesante, Annali Sper. Agr. N.S. 11: Suppl.: CCLXI–CCLXV, 1957, and by M. B. Ellis, Dematiaceous Hyphomycetes, Commonwealth Mycological Institute, Kew, Surrey, England, p. 28, 1971. As used herein throughout the specification and claims, the term "Scytalidium catalase" gene or nucleic acid sequence is intended to encompass a catalase (and sequence encoding same) of either of the two species of the complex. It also is intended to encompass catalases of isolates which have previously been assigned to other taxonomic categories, but which are properly assigned to the Humicola-Scytalidium complex as defined herein. For example, the complex includes the thermophilic hyphomycetes previously classified as Humicola grisea var. thermoidea Cooney & Emerson, H. insolens Cooney & Emerson, and Torula thermophila Cooney Emerson, described in D. G. Cooney and R. Emerson, Thermophilic Fungi. An account of their biology, activities and classification, San Francisco, Freeman, 1964. Strains of the members of the complex are widely publicly available at recognized depositories, e.g., in the American Type Culture Collection, 12301 Parklawn Drive, Rockville, Md. (ATCC); Centraal Bureau voor Schimmelcultures, Osterstraat 1, 3740 AG Baarn, Netherlands (CBS); University of Alberta Microfungus Collection (UAMH) and CAB International Mycological Institute (IMI). Examples of available strains from which useful genetic material can be obtained are ATCC 28085, ATCC 48409, CBS 671.88(Scytalidium thermophilum) and UAMH 2925, IMI 158747 and ATCC 34627 (Humicola insolens).

As described below, to isolate a Scytalidium catalase gene, genomic DNA of S. thermophilum is used as a template in a PCR reaction with two degenerate primers based on partial peptide sequences obtained from an isolated S. thermophilum catalase protein. A 1.1 kb band is obtained and cloned into a plasmid to produce pDM117. A 1.1 kb HindIII/NotI fragment is isolated from this plasmid, labelled and used to screen genomic libraries.

Figure 3:
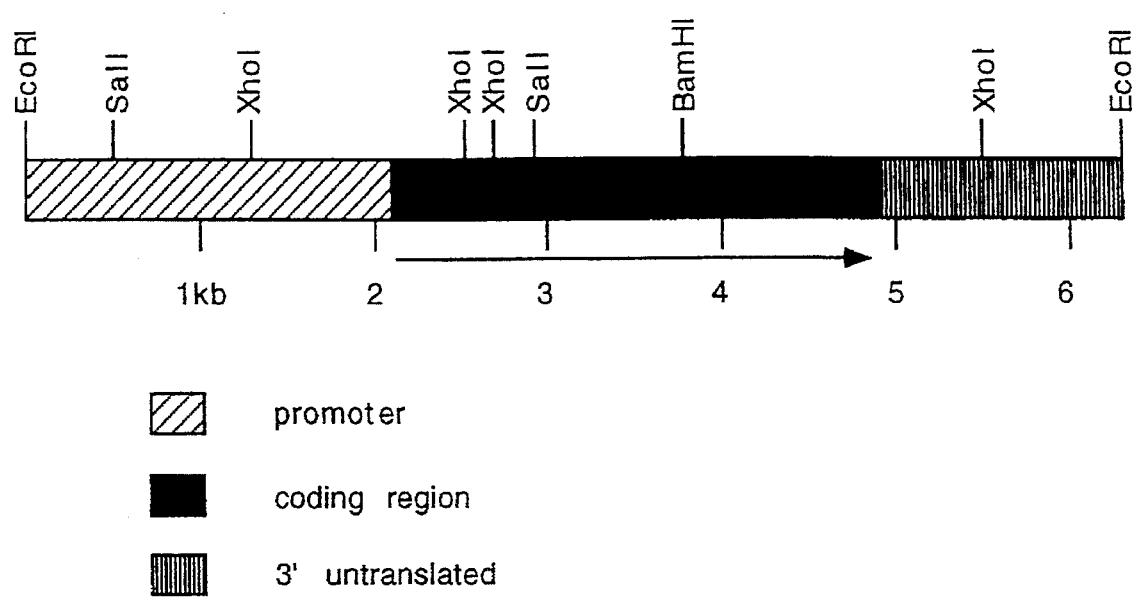
FIG. 3 illustrates the restriction map of a S. thermophilum genomic catalase clone.

Screening of a *S. thermophilum* genomic library yields strongly hybridizing bands. A genomic EMBL4 library is then prepared and DNA preparations made from putative positive clones. These are probed with the 1.1 kb fragment and a hybridizing 6.3 kb EcoRI fragment is identified (FIG. 3); this fragment is subsequently shown to contain the entire coding region of the catalase gene as well as promoter and untranslated sequence. Screening of a cDNA library using PCR with exact match primers yields cDNA subclones which confirm the genomic sequence.

The catalase is encoded by 2791 base pairs, with 7 introns (FIG. 4). The predicted amino acid sequence of 717 residues appears to encode a prepro-catalase with a 19 amino acid signal sequence, and a 17 amino acid proregion. The predicted amino acid sequence also correlates well with the amino acid sequence determined from peptides derived from sequencing of the native protein. When compared with known catalase gene sequences, the DNA sequence is closest to that of *A. niger*, showing a 61% and 57% homology at the nucleotide and amino acid levels, respectively.

Figure 6:
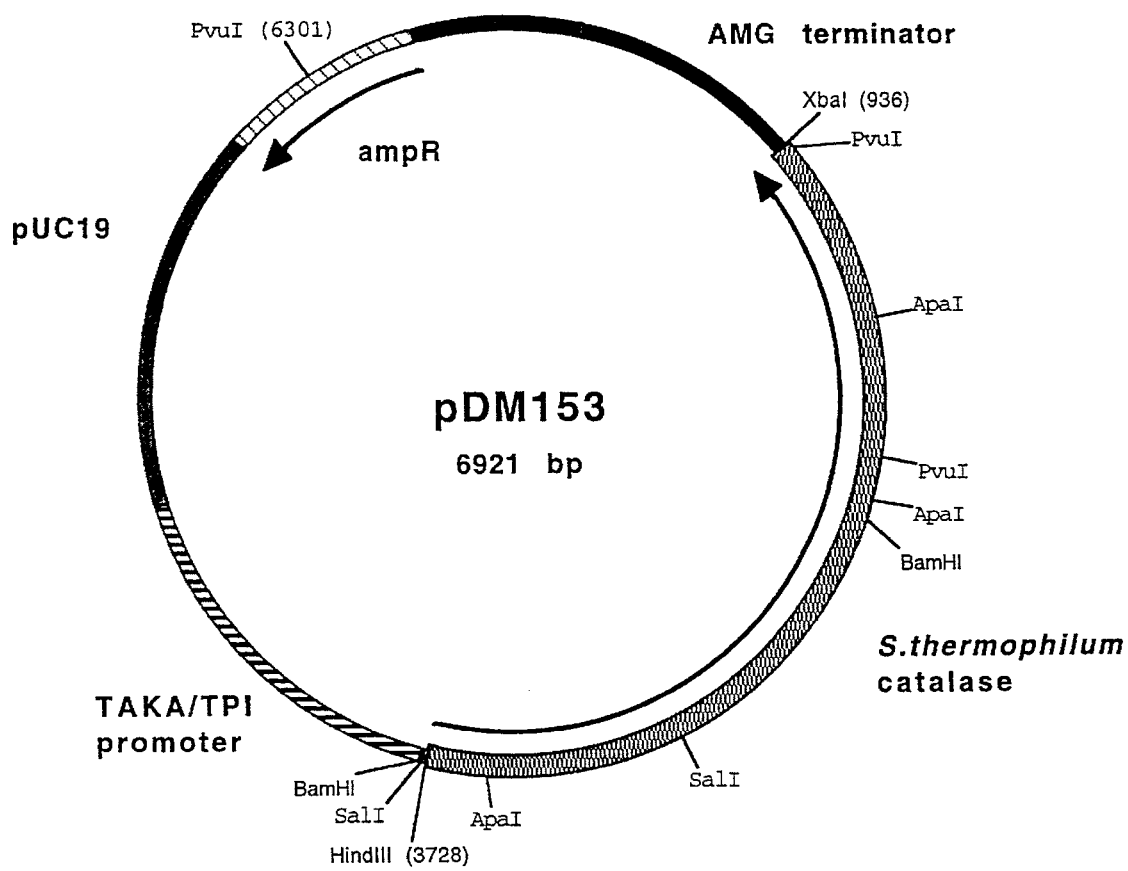
FIG. 6 illustrates an expression construct, pDM153 for the S. thermophilum catalase.
Figure 7:
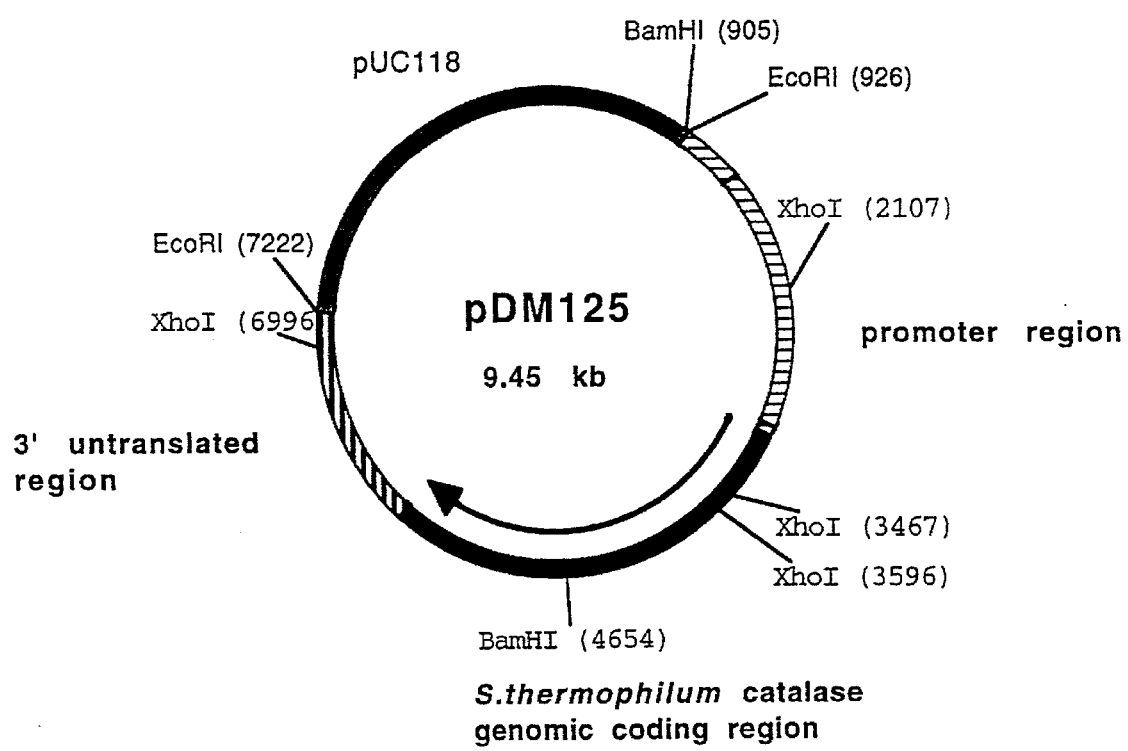
FIG. 7 illustrates the 6.3 kb Scytalidium genomic fragment containing the catalase gene, which is subcloned into Bluescript pSK-, now called plasmid pDM125.

The gene is PCR modified at both the 5' and 3' ends to introduce restriction sites. Three catalase fragments are ligated together and inserted between an *A. oryzae* TAKA amylase/TPI (triose phosphate isomerase fusion promoter (as described in WO 94/23022) and the *A. niger* amyloglucosidase (AMG) terminator in a plasmid (FIG. 6). This plasmid is cotransformed with an amdS selection plasmid into an *A. oryzae* host cell, as described in WO 91/17243, and grown on plates for three days. Several transformants show significantly more catalase activity than untransformed controls. The best producers are cultured in shake flasks and grown for 5 days. The best producer of this group makes 12,800 CIU/ml. Yield of catalase can be improved by culturing the host cell in a medium containing heme or a heme containing material, as described in copending U.S. Ser. No. 08/284,566, the contents of which are incorporated herein by reference.

According to the invention, a Scytalidium gene encoding a catalase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a catalase gene to be used according to the invention is operably linked to the control sequences in the proper reading frame.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), or the promoters of the *Bacillus subtilis* xylA and xylB genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase, TAKA-amylase-TPI fusion, and glaA promoters.

The expression vector of the invention may also comprise a suitable transcription terminator and, in eukaryotes, polyadenylation sequences operably connected to the DNA sequence encoding the catalase of the invention. Termination and polyadenylation sequences may suitably be derived from the same or different sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracycline resistance. Examples of Aspergillus selection markers include amdS, pyrG, argB, niaD, sC, and hygB a marker giving rise to hygromycin resistance. Preferred for use in an Aspergillus host cell are the amdS and pyrG markers of *A. nidulans* or *A. oryzae*. A frequently used mammalian marker is the dihydrofolate reductase (DHFR) gene. Furthermore, selection may be accomplished by co-transformation, e.g. as described in WO 91/17243.

It is generally preferred that the expression gives rise to a product that is extracellular. The catalases of the present invention may thus comprise a preregion permitting secretion of the expressed protein into the culture medium. If desirable, this preregion may be native to the catalase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces, Pichia or Schizosaccharomyces, e.g. *Saccharomyces cerevisiae*. Useful filamentous fungi may be selected from a species of Aspergillus, e.g. *Aspergillus oryzae* or *Aspergillus niger*. Alternatively, a strain of a Fusarium species, e.g. *F. oxysporum*, or *F. graminearum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

The present invention thus provides a method of producing a recombinant catalase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the catalase of the invention. Suitable media are available from commercial suppliers or may be prepared according to published formulae (e.g. in catalogues of the American Type Culture Collection).

The resulting enzyme may be recovered from the medium by conventional procedures including separating the cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of catalase is achieved in a fungal host cell, such as Aspergillus. As described in detail in the following examples, the catalase gene is ligated into a plasmid containing the *Aspergillus oryzae* TAKA α-amylase/TPI promoter, and the *Aspergillus nidulans* amdS selectable marker. Alternatively, the amdS may be on a separate plasmid and used in co-transformation. The plasmid (or plasmids) is used to transform an Aspergillus species host cell, such as *A. oryzae* or *A. niger* in accordance with methods described in Yelton et al. (PNAS USA 81: 1470–1474, 1984).

Those skilled in the art will recognize that the invention is not limited to use of the nucleic acid fragments specifically disclosed herein, for example, in FIG. 4. It will also be apparent that the invention encompasses those nucleotide sequences that encode the same amino acid sequences as depicted in FIG. 4, but which differ from those specifically depicted nucleotide sequences by virtue of the degeneracy of the genetic code. Also, reference to FIG. 4, in the specification and the claims will be understood to encompass both the genomic sequence depicted therein as well as the corresponding cDNA and RNA sequences, and the phrases "nucleic acid construct" and "nucleic acid sequences" as used herein will be understood to encompass all such variations. "nucleic acid construct" shall generally be understood to mean a nucleic acid molecule, either single- or double-stranded, which may be isolated in partial form from a naturally occurring gene or made synthetically from a naturally occurring gene template, or which has been modified to contain segments of nucleotides which are combined and juxtaposed in a manner which would not otherwise exist in nature.

In addition, the invention also encompasses other Scytalidium catalases, including alternate forms of catalase which may be found in *S. thermophilum* and as well as catalases which may be found in other fungi which are synonyms or fall within the definition of *Scytalidium thermophilum* as defined by Straatsma and Samson, 1993, supra. These include *S. indonesiacum, Torula thermophila, Humicola brevis* var. thermoidea, *Humicola brevispora, H. grisea* var. thermoidea,*Humicola insolens*, and *Humicola lanuginosa* (also known as *Thermomyces lanuginosus*). The invention also provides the means for isolation of catalase genes from other species of Scytalidium, such as *S. acidophilum, S. album, S. aurantiacum, S. circinatum, S. flaveobrunneum, S. hyalinum, S. lignicola*, and *S. uredinicolum*. Identification and isolation of catalase genes from sources other than those specifically exemplified herein can be achieved by utilization of the methodology described in the present examples, with publicly available Scytalidium strains. Alternately, the sequence disclosed herein can be used to design primers and/or probes useful in isolating catalase genes by standard PCR or Southern hybridization techniques, using the same publicly available strains. Examples of such publicly available strains include, from the American Type Culture Collection, ATCC 16463, 28085, 36346, 48409, 66938 (*S.

thermophilum); 24569 (S. acidophilum); 16675 (S. album); 22477 (S. aurantiacum); 66463(S. circinatum); 13212 (S. flavo-brunneum); 52297 (S. fulvum); 38906 (S. hyalinum); 46858 (S. indonesiacum); 18984 (S. indonesiacum); 32382 (S. uredinaolum); from the International Mycological Institute (IMI; United Kingdom), IMI 243 118 (S. thermophilum); from Centraal bureau voor Schimmelcultures (CBS; Netherlands) CBS 183.81, 671.88 (S. thermophilum) 367.72 (S. acidophilum); 372.65 (S. album); 374.65 (S. aurantiacum); 654.89 (S. circinatum); 244.59 (S. flavo-brunneum); 145.78 (S. hyalinum); 259.81 (S. indonesiacum); 233.57 (S. lignicola); 171.40 (S. terminale); 616.84 (S. muscorum); from Deutsche Sammlung yon Mikroorganismenn und Zellkulturen (DSM; Germany) DSM 2842 (S thermophilum); DSM 2695 (S. lignicola). The invention also encompasses any variant nucleotide sequence, and the protein encoded thereby, which protein retains at least about an 80%, preferably about 85%, and most preferably at least about 90–95% homology with the amino acid sequence depicted in FIG. 1, and which qualitatively retains the catalase activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by conducting a standard titanium color method, such as is described in the present examples.

The invention is further illustrated by the following non-limiting examples.

EXAMPLES

I. Materials and Methods

A. Generation of PCR Probes

Two degenerate PCR primers are designed based upon partial peptide sequence derived from the native S. thermophilum protein. The forward primer (PmeST5) corresponds to the N-terminal peptide sequence. The reverse primer (St3.2not) corresponds to the region from amino acids 265 to 271 (FIG. 1). 200 pmoles of each degenerate primer and 120 ng S. thermophilum genomic DNA are added per 100 μl reaction. The Taq polymerase and PCR buffer are obtained from Boehringer Mannheim. A linear amplification is performed by adding only primer St3.2not, denaturing the DNA 3 minutes at 95° C., then running 10 cycles of [95° C. 30 seconds/48° C. 1 minute/72° C. 1 minute]. Primer PmeST5 is then added and the following PCR reaction is run: 95° C., 3 minutes then 25 cycles of [95° C., 30 seconds/37° C., 40 seconds/72° C., 1 minute]. The resulting 1.1 kb band is isolated on a 1% agarose gel in TAE (0.04M Tris-acetate, 0.001M EDTA, pH 8.0) and cloned into EcoRV/NotI digested pBluescript SK-(Stratagene Cloning Systems, Lajolla, Calif.) to create pDM117. A 1.1 kb HindIII/NotI catalase fragment is gel purified from pDM117 and labelled in a PCR reaction containing digoxigenin-labeled deoxyuridine-triphosphate (dUTP) using the primers described above. Reaction conditions are: 95° C., 3 minutes, then 35 cycles of [95° C., 30 seconds/48° C., 1 minute/72° C., 1 minute]. This digoxigenin (DIG) labelled probe is used to screen genomic libraries.

B. Genomic Library Preparation

2. DNA Libraries and Identification of Catalase Clones

Genomic DNA libraries are constructed in the bacteriophage cloning vector λ-EMBL4 (J. A. Sorge, in Vectors, A Survey of Molecular Cloning Vectors and Their Uses, Rodriguez et al., eds, pp. 43–60, Butterworths, Boston, 1988). Briefly, total cellular DNA is partially digested with Sau3A and size-fractionated on low-melting point agarose gels. DNA fragments migrating between 9 kb and 23 kb are excised and eluted from the gel using β-agarase (New England Biolabs, Beverly, Mass.). The eluted DNA fragments are ligated with BamHI-cleaved and dephosphorylated λ-EMBL4 vector arms, and the ligation mixtures are packaged using commercial packaging extracts (Stratagene, LaJolla, Calif.). The packaged DNA libraries are plated and amplified on Escherichia coli K802 cells.

C. Genomic Library Screening

Lambda phage are plated with E. coli K802 cells onto LB plates with NZY top agarose. Plaque lifts are made to nylon membranes (Hybond N, Amersham) using standard techniques (Sambrook et al., Molecular Cloning. A Laboratory Manual. 2nd ed. Cold Spring Harbor, 1989). DNA is bound to membranes by UV crosslinking. Filters are hybridized with the 1.1 kb DIG labelled probe described above. Hybridization and detection of catalase clones are performed using techniques described in the Boehringer Mannheim Genius™ System User's Guide. Hybridizations are performed at 65° C. in 5XSSC, 0.1% L-lauroylsarcosine, 0.02% SDS, 1% blocking reagent for nucleic acid hybridization (Boehringer Mannheim). The concentration of DIG labelled probe used is 5 ng/ml hybridization solution. Hybridizing DNA is immunodetected with an alkaline phosphatase-conjugated anti-digoxigenin antibody and visualized with Lumiphos 530, a chemiluminescent substrate (Boehringer Mannheim). DNA preparations are made from putative positive lambda clones using the Qiagen Lambda Midi kit (QIAGEN, Inc.).

D. RNA and cDNA Preparation

RNA and cDNA libraries are prepared from S. thermophilum strain A1065(ATCC 28085). Total RNA is prepared by extraction of ground frozen mycelia with guanidium thiocyanate followed by ultracentrifugation through a 5.7M CsCl cushion. Poly (A)+RNA isolated by oligo (dT)-cellulose affinity chromatography is used to generate cDNA by the RNAse H method using the hairpin modification method (Sambrook et al., Molecular Cloning: A Laboratory Manual, 1989; U.S. Ser. No. 08/398,489, the contents of which are incorporated herein by reference). The cDNA is ligated to BstXI linkers and size selected by agarose gel electrophoresis with a cutoff at 0.7 kb. The resulting cDNA is ligated into yeast expression plasmid pYES2(Invitrogen Corporation) and cloned into E. coli strain DH12S. The resulting library is divided into three pools with approximately 50,000 clones per pool.

E. cDNA Fragment Cloning

Three 125 ml shakeflasks containing 25 ml 2xYT(16 g/l bacto-tryptone, 10 g/l bacto-yeast extract, 5 g/l NaCl, pH 7.0), 50 μg/ml carbenicillin are inoculated with a loop full of frozen pYES2 library, one flask for each pool. Cultures are grown overnight at 37° C. Plasmid preps are made from 20 ml of culture using Qiagen tip 100 and standard Qiagen techniques. DNA is dissolved initially in 100 μl TE (10 mM Tris, DH 8.0, 1 mM EDTA, pH 8.0). DNA concentration is determined by absorbance at 260 nm and samples are diluted to a final concentration of 0.5 mg/ml. 100 µl PCR reactions using 250 ng DNA as template and 56 pmoles of gene specific primers(forward primer, 5' CCGCGGCGTC-CTTTCTGA 3'; reverse primer, 5' GATCTTTGTCGGGTC-CAG 3') are prepared. The PCR reaction buffer and Taq polymerase are obtained from Boehringer Mannheim. As a positive control a reaction using 190 ng genomic S. thermophilum DNA is prepared. All reactions are amplified by denaturing at 95° C. for 3 minutes followed by 30 cycles of [95° C., 30 seconds; 55° C., 1 minute; 72° C., 1 minute]. Subsequent PCR reactions used 250 ng pYES2 pool 5 DNA as template and the reaction conditions described above. Several combinations of catalase and pYES2 vector primers are used to generate five cDNA fragments which cover the entire coding region of the gene (FIG. 2). These fragments are subcloned into vector pCRII using Invitrogen's TA cloning kit.

F. Sequence Analysis

In general, nucleotide sequences are determined using Taq polymerase cycle sequencing with fluorescent labelled nucleotides (Giesecke et al., J. Virol. Methods 38: 47–60, 1992, ). Occasionally, reactions using bacteriophage T7 DNA polymerase (PRISM™ T7 Terminator Kit, Applied Biosystems) are employed to obtain clearer sequence in G/C rich regions. Reactions are analyzed using an Applied Biosystems automatic DNA sequencer (Model 363/A, version 1.2.0).

G. Transformation of A. oryzae Host Cells

Four wells of a 24 well tissue culture plate are filled with 500 µl YEG (5 g/l yeast extract, 20 g/l sucrose)+1M sucrose medium. Each well is inoculated with 2–5×10$^6$ conidia and the plate is incubated 16 hours at 37° C. without shaking. The media is removed with a 1 ml piper tip and 500 µl Novozym™ solution [OM buffer(1.2M MgSO$_4$ buffered to pH 5.8 with 1M Na$_2$HPO$_4$), 5 mg/ml Novozym™ 234, 1 mg/ml BSA] is added. The fungal mat is dispersed by pipetting repeatedly with a cut-off 1 ml piper tip. The plate is incubated at 34° C., 90 rpm until protoplasting is complete (approximately 1 hour). The protoplasts are transferred to a microfuge tube and washed three times with 1 ml STC(1.2M sorbitol, 10 mM CaCl$_2$, 10 mM Tris-HCl, pH 7.5). The protoplasts are suspended at a concentration of 5×10$^7$–1×10$^8$/ml in STC:SPTC:DMSO (8:2:0.1). [STC, as above; SPTC:40% PEG 4000, 0.8M sorbitol, 50 mM CaCl$_2$, 50 mM Tris-HCl, pH 8.0]

5 µg of plasmids pDM153 (catalase expression plasmid) and pToC90(amdS selection) are added to 100 µl protoplasts in a Falcon tube (17×100 mm size). 1 ml of SPTC is added. Samples are incubated 20 minutes at room temperature. Approximately 370 µl protoplast/SPTC mixture is added to 15 ml of overlay agarose that had been tempered to 50° C. Each transformation aliquot is plated onto a 150 mm plate of selective media that contains 1M sucrose. Acetamidase (amdS) positive transformants are selected on COVE minimal medium with acetamide as the sole nitrogen source. Transformants are incubated at 37° C.

H. Expression Construct

The 5' end of the gene is modified using PCR to introduce a HindIII site directly upstream of the translational start. At the 3' end of the gene, an XbaI site is introduced directly after the termination codon using PCR. Three catalase genomic DNA fragments (HindIII/ApaI; ApaI/SalI; SalI/XbaI; are ligated together and inserted between the A oryzae TAKA amylase/TPI (triose phosphate isomerase) fusion promoter and the A. niger amyloglucosidase(AMG) terminator in plasmid pMT1560(described in WO 94/23022). The resulting expression construct, called pDM153, is illustrated in FIG. 6.

I. Expression of Catalase in A. oryzae

Transformants are transferred to a 24 well tissue culture plate containing 1 ml COVE agar per well and incubated at 37° C. Conidia are suspended in 0.5 ml 0.01% Tween 20. Twenty-four well plates containing 1 ml M400Da medium per well are inoculated with 15 µl conidia suspension. M400Da medium contains maltodextrin 50.0g/l ; MgSo$_4$.7H$_2$O, 2.0 g/l; KH$_2$PO$_4$, 2.0 g/l; citric acid, 4.0 g/l; yeast extract, 8.0 g/l, urea, 2.0 g/l; trace metal solution I, 0.5 ml/l [trace metal solution: ZnSO$_4$.7H$_2$O 14.3 g/l; CuSO$_4$.5H$_2$O, 2.5 g/l; NiCl$_2$.6H$_2$O, 0.5 g/l; FeSO$_4$.7H$_2$O, 13.8 g/l; MnSO$_4$.H$_2$O, 8.5 g/l; citric acid, 3.0 g/l]; pH adjusted to 6.0 with 5N NaOH. These plates are incubated at 37° C., 100 rpm for 3 days in a lexan culture box to maintain the humidity level and minimize loss of culture volume. Shakeflask cultures are prepared by adding 150 µl spore purified conidia stock to 25 ml M400Da medium in 125 ml polypropylene flasks. Cultures are incubated 5 days at 37° C. 100 rpm. supernatants are recovered and assayed for catalase activity.

J. Catalase Assays

Catalase mediated degradation of hydrogen peroxide is measured by a modification of the titanium color method of Patti and Bonet-Maury (Bull. Soc. Chem. Biol. 35: 1177, 1953). The titanium reagent is made by mixing 1 g TiO$_2$ and 10 g K$_2$SO$_4$, digesting on a mantle heater for 2–3 hours at 180°–220° C. in 150 ml of concentrated H$_2$SO$_4$, cooling, and then diluting to 1.5 l with deionized water. Stock 16 mM H$_2$O$_2$ solution is prepared in 10 mM Na phosphate buffer, DH 7.0. The assay consists of mixing 25 µl of sample and 25 µl of the H$_2$O$_2$ solution in microtiter wells (96 well plate) and incubating for 5 minutes at room temperature. 200 µl of the titanium reagent is added and the absorbance at 405 nm is read using a Thermomax microplate reader from Molecular Devices. Standard A. niger catalase (Sigma) is diluted to concentrations ranging from 0.2 CIU/ml to 3.0 CIU/ml in 10 mM Na phosphate buffer, pH 7.0. One CIU causes decomposition of one µmole of H$_2$O$_2$ per minute under the conditions described above.

Catalase is also analyzable by UV. Supernatants from fungal cultures are centrifuged in a microfuge at maximum speed for 5 minutes. One ml of phosphate buffer (50 mM KPO$_4$ buffer, pH 7.0) is transferred to a reference cuvette. The catalase standard is an Aspergillus niger catalase. Reaction solution is prepared by adding 0.09 ml 30% H$_2$O$_2$ stock solution (SIGMA) to 50 ml phosphate buffer, the absorbance read at 240 nm, and the absorbance adjusted to 0.5 to 0.55. Catalase-containing supernatants are diluted with phosphate buffer to yield an approximate concentration of 100 to 300 CIU/ml. 25 µl of the diluted supernatant is added to 975 µl of reaction solution, mixed and $\Delta A_{240\,nm}$ is recorded. Readings are taken, on a Shimadzu dual beam spectrophotometer (Shimadzu Scientific Instruments, Inc., Columbia, Md.) for at least 15 seconds at one second intervals, and the $\Delta A_{240}$/minute is calculated. The activity in CIU/ml is calculated according to the following formula: CIU/ml=$\Delta A_{240}$/minute× 23×dilution factor(s). One CIU is defined as the amount of catalase which will decompose one µmole of H$_2$O$_2$ per minute in 50 mM KPO$_4$ buffer (pH 7.0) at 25° C., at a starting H$_2$O$_2$ concentration of 11.5 to 12.0 mM.

II. Results and Discussion

A. Library Screening (1). cDNA. DNA preparations from the pYES2 library is screened by PCR for the presence of the catalase gene. Exact match primers(forward primer: 5' CCGCGGCGTC- CTTTCTGA 3' (SEQ ID No. 5); reverse primer: 5' GATCTTTGTCGGGTCCAG 3'SEQ. ID No. 6) yields a 0.6 kb catalase fragment from the pYES2 library DNA. Primers which are used to sequence genomic clones are used as PCR primers to generate five small fragments of cDNA from the pYES2 library. FIG. 2 shows the cDNA subclones obtained. After subcloning into a TA vector, these fragments are sequenced using M13 and catalase specific primers. The cDNA sequence obtained verifies the genomic sequence and locations of introns.

(2). Genomic DNA. Approximately 40,000 phage are plated from the S. thermophilum A 1065 genomic EMBL4 library. DNA preparations are made from six out of seven putative positive lambda clones using the Qiagen Lambda Midi Kit (QUIAGEN, Inc.). These preps are digested with restriction enzymes and subjected to Southern blot analysis. The blot is probed with the 1.1 kb DIG labelled catalase fragment using the hybridization conditions described above. Three independent clones are identified. A hybridizing 6.3 kb EcoRI fragment includes the entire 2.8 kb coding region of the catalase gene, 2.1 kb of upstream (promoter) sequence and approximately 1.4 kb of 3' untranslated sequence. This EcoRI fragment is subcloned into Bluescript pSKhu − to create plasmid pDM125.

B. DNA Sequence Analysis

The cloned S. thermophilum catalase is encoded by 2791 base pairs containing 7 introns of length 131, 79, 76, 153, 53, 54, and 94 base pairs. The translated sequence is shown in FIG. 4. The predicted amino acid polypeptide of the prepro-catalase is 717 residues. Prepro-catalase consists of a putative 19 amino acid signal sequence, based on the rules of yon Heijne (Nucl. Acids Res. 14: 4683–4690, 1986). Amino acid sequence analysis performed on the native protein indicates that the N-terminus of the mature protein begins at amino acid 37, showing that the protein also contains a putative 17 amino acid proregion. The catalase contains three potential N-linked glycosylation sites located in the mature region of the polypeptide. The predicted molecular weight of the mature catalase (without glycosylation) is 75 kD. A comparison of the DNA translated amino acid sequence to the peptides derived from protein sequencing is shown in FIG. 5. The correlations are good, and any differences observed may be due to ambiguities in protein sequencing.

When compared with known catalase sequences, the DNA sequence of the S. thermophilum catalase cloned from strain A1065 shows the closest homology with the A. niger catR catalase; the nucleic acid sequence is 61% identical to the DNA sequence of the A. niger catalase R gene. The two catalases are 57% identical on the amino acid level. However, the organization of these two genes is quite different. The S. termophilum catalase coding region is interrupted by seven introns, whereas the A. niger catR gene contains only four introns. The first two introns are in similar positions in the two genes, but none of the remaining introns are conserved.

C. Expression in A. oryzae

An A. oryzae strain is cotransformed with catalase construct pDM153 and plasmid pToC90(amdS selection) as described above. Thirty-six transformants are grown in M400Da medium in 24 well plates for 3 days. Supernatants are collected and assayed using the titanium color method. Several of the transformants exhibit significantly more catalase activity than the untransformed control culture. The highest expresser makes approximately 1200 CIU/ml. The four best producers are spore purified twice. Shake flasks containing M400Da medium are inoculated and grown five days at 37° C., 100 rpm. Samples are taken at 4 and 5 days and assayed using the titanium color method. The best producer in shake flasks makes 12,800 CIU/ml.

The best producer is used to express the Scytalidium catalase in a fermentation medium, using a fed batch process in a 3 liter laboratory fermentor. The fermentation media have the following compositions:

| Tanks: | Nutriose 725* | 30 g/l (autoclaved separately) |
|---|---|---|
| | $(NH_4)_2HPO_4$ | 5 g/l |
| | yeast extract | 5 g/l |
| | $MgSO_4.7H_2O$ | 2 g/l |
| | $KH_2PO_4$ | 2 g/l |
| | citric acid.$H_2O$ | 4 g/l |
| | $K_2SO_4$ | 3 g/l |
| | $CaCl_2.2H_2O$ | 2 g/l |
| | trace metal sol.** | 0.5 ml/l |
| | pluronic | 1.0 ml/l |
| | hemoglobin | 20 g/l |

*maltose syrup (Roquette Corporation, Gurnee, IL)
**$ZnSO_4.7H_2O$, 14.3 g/l; $CuSO_4.5H_2O$, 2.5 g/l; $NiCl_2.6H_2O$, 0.5 g/l; $FeSO_4.7H_2O$; 13.8 g/l; $MnSO_4.H_2O$, 8.5 g/l; citric acid, 3.0 g/l Hemoglobin is dissolved separately in 0.1N NaOH. Salts are added while maintaining the medium at pH 10.5. The volume is brought to 1.8 l+5% with tap water, and autoclaved 60 minutes at 125° C. The pH is adjusted to 7.6 with $H_3PO_4$.

| Feed: | Nutriose 725 | 400 g/kg |
|---|---|---|
| | citric acid.$H_2O$ | 1 g/kg |
| | yeast extract | 5 g/l (autoclaved separately) |
| | urea | 10 g/kg |
| | pluronic | 1 ml/kg |

The mixture is adjusted to 1.8 kg+5% with tap water and the pH adjusted to 4.5 before autoclaving.

To produce the inoculum, one ml of spore suspension (approximately $10^7$ spores) of the strain described above is added to 100 ml of MY50 medium (50 g/l maltodextrin, 2 g/l $MgSO_4.7H_2O$, 10 g/l $KH_2PO_4$, 2 g/l $K2SO_4$, 2 g/l citric acid, 10 g/l yeast extract, 0.5 ml trace metals, 2.0 g/l urea) in a 500 ml polypropylene flask and the culture grown for 24 hours at 34° C., at 200 rpm. 60 ml of shakeflask culture is added to 1.8 l medium in the 3 liter fermentor, and fermentation carried out at 34° C. pH 7.6(controlled with NaOH, $H_3PO_4$), DO>20% (controlled by agitation of 800–1200 rpm) with aeration of 1 vvm. The feed is started when DO has dropped, at approximately 20 hours. The feed is started at 8 g/tank/hour, and raised to 12 g/tank/hour dependent on DO. Under these conditions, yield of catalase increases significantly relative to the yield obtained in shake flasks.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604 and given the following accession number:

| Deposit | Accession Number |
|---|---|
| E. coli containing pDM125 (a 6.3 kb EcoRI genomic fragment cloned into a pBluescript SK-plasmid) | NRRL B-21426 |

What we claim is:

1. A nucleic acid construct comprising a nucleic acid sequence encoding a catalase endogenous to the genus Scytalidium wherein the nucleic acid coding sequence is selected from the group consisting of:

(a) a naturally-occurring catalase gene isolated from a Scytalidium strain, wherein the naturally-occurring catalase gene hybridizes with at least one coding exon of SEQ ID NO:1 at a stringency defined by 65° C., five-fold SSC, 0.1% lauroylsarcosine, 0.02% SDS and 1% blocking reagent; and, (b) a nucleic acid sequence encoding the amino acid sequence of an endogenous Scytalidium catalase.

2. The construct of claim 1 wherein the catalase is endogenous to the species of Scytalidium thermophilum.

3. The construct of claim 1 wherein the nucleic acid sequence encodes the amino acid sequence set forth in SEQ ID NO:2.

4. The construct of claim 1 wherein the nucleic acid sequence has the sequence set forth in SEQ ID NO:1.

5. The construct of claim 1 wherein the nucleic acid sequence is the catalase-encoding nucleic acid sequence comprised by plasmid pDM125 in the deposit NRRL B-21426.

6. A recombinant vector comprising the nucleic acid construct of claim 1.

7. The vector of claim 6 wherein said nucleic acid construct comprises a promoter sequence operably linked to the catalase-encoding nucleic acid sequence.

8. The vector of claim 7 in which the promoter is a fungal or yeast promoter.

9. The vector of claim 8 in which the promoter is the TAKA amylase promoter or the triose phosphate isomerase promoter of Aspergillus oryzae, or a fusion thereof.

10. The vector of claim 7 which also comprises a selectable marker.

11. The vector of claim 10 in which the selectable marker is selected from the group consisting of amdS, pyrG, argB, niaD, sC, and hygB.

12. The vector of claim 11 in which the selectable marker is the amdS marker of Aspergillus nidulans or Aspergillus oryzae, or the pyrG marker of Aspergillus nidulans, Aspergillus niger, Aspergillus awamori, or Aspergillus oryzae.

13. The vector of claim 9 which comprises both the TAKA amylase promoter of Aspergillus oryzae and the amdS or pyrG marker of Aspergillus nidulans or Aspergillus oryzae.

14. A transformed host cell comprising the nucleic acid construct of claim 1.

15. The host cell of claim 14 which is a fungal cell.

16. The host cell of claim 15 which is an Aspergillus cell.

17. The host cell of claim 14 in which the construct is integrated into the host cell genome.

18. The host cell of claim 14 in which the nucleic acid construct is comprised by a vector.

19. The host cell of claim 14 which comprises a construct comprising a sequence encoding the amino acid sequence depicted in SEQ ID NO. 2.

20. A method for producing a catalase enzyme which comprises culturing a host cell transformed with the nucleic acid construct of claim 1 in a culture medium under conditions permitting the expression of the enzyme, and recovering the catalase from the culture medium.

21. A method according to claim 20 in which the catalase is secreted into the culture medium.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 2794 base pairs
        ( B ) TYPE: nucleic acid
        ( C ) STRANDEDNESS: single
        ( D ) TOPOLOGY: linear ( i x ) FEATURE:
        ( A ) NAME/KEY: intron
        ( B ) LOCATION: 283..413

( i x ) FEATURE:
        ( A ) NAME/KEY: intron
        ( B ) LOCATION: 618..696

( i x ) FEATURE:
        ( A ) NAME/KEY: intron
        ( B ) LOCATION: 718..793

( i x ) FEATURE:
        ( A ) NAME/KEY: intron
        ( B ) LOCATION: 956..1108

( i x ) FEATURE:
        ( A ) NAME/KEY: intron
        ( B ) LOCATION: 1166..1218

( i x ) FEATURE:
        ( A ) NAME/KEY: intron
        ( B ) LOCATION: 1789..1842

( i x ) FEATURE:
        ( A ) NAME/KEY: intron
        ( B ) LOCATION: 2671..2764

( i x ) FEATURE:
        ( A ) NAME/KEY: CDS
        ( B ) LOCATION: join(1..282, 414..617, 697..717, 794..955, 1109
            . . 1165, 1219..1788, 1843..2670, 2765..2791)

( x i ) SEQUENCE DESCRIPTION: SEQ ID NO:1:

```
ATG AAC AGA GTC ACG AAT CTC CTC GCC TGG GCC GGC GCG ATA GGG CTC      48
Met Asn Arg Val Thr Asn Leu Leu Ala Trp Ala Gly Ala Ile Gly Leu
 1               5                  10                  15

GCC CAA GCA ACA TGT CCC TTT GCG GAC CCT GCC GCT CTG TAT AGT CGT      96
Ala Gln Ala Thr Cys Pro Phe Ala Asp Pro Ala Ala Leu Tyr Ser Arg
                 20                  25                  30

CAA GAT ACT ACC AGC GGC CAG TCG CCA CTT GCA GCA TAC GAG GTG GAT     144
Gln Asp Thr Thr Ser Gly Gln Ser Pro Leu Ala Ala Tyr Glu Val Asp
                 35                  40                  45

GAC AGC ACC GGA TAC CTG ACC TCC GAT GTT GGC GGG CCC ATT CAG GAC     192
Asp Ser Thr Gly Tyr Leu Thr Ser Asp Val Gly Gly Pro Ile Gln Asp
     50                  55                  60

CAG ACC AGC CTC AAG GCA GGC ATC CGG GGT CCG ACC CTT CTT GAG GAC     240
Gln Thr Ser Leu Lys Ala Gly Ile Arg Gly Pro Thr Leu Leu Glu Asp
 65                  70                  75                  80

TTT ATG TTC CGC CAG AAG ATC CAG CAC TTC GAC CAT GAA CGG             282
Phe Met Phe Arg Gln Lys Ile Gln His Phe Asp His Glu Arg
                 85                  90

GTAAGGACAT AATGCTCACA CGAGCGGCTG CGTGCCACC TATTTCCGAG ACATTGGGCT    342

GGCTGGCTGG CTGTGACTGC TTGAGTTTGG GGACATACGG AGTACCTTAC TGACGCGCTG   402

AACCACTCCA G GTT CCC GAA AGG GCG GTC CAT GCT CGA GGC GCT GGA GCA    452
```

```
                Val Pro Glu Arg Ala Val His Ala Arg Gly Ala Gly Ala
                 95                 100                     105
CAC GGG ACC TTC ACG AGT TAC GCC GAC TGG AGT AAC ATC ACC GCG GCG    500
His Gly Thr Phe Thr Ser Tyr Ala Asp Trp Ser Asn Ile Thr Ala Ala
        110             115                 120

TCC TTT CTG AAC GCC ACT GGA AAG CAG ACG CCG GTG TTT GTC CGG TTC    548
Ser Phe Leu Asn Ala Thr Gly Lys Gln Thr Pro Val Phe Val Arg Phe
    125             130                 135

TCG ACC GTT GCT GGG TCT CGA GGG AGC GCA GAC ACG GCG AGA GAC GTT    596
Ser Thr Val Ala Gly Ser Arg Gly Ser Ala Asp Thr Ala Arg Asp Val
140             145                 150                 155

CAT GGT TTC GCG ACG CGG TTT GTAAGTTTTG TTGTGTTTCA TTCGTTCCGG       647
His Gly Phe Ala Thr Arg Phe
                160

TCTGTAGAGG AGGGTTAGGA TATGAGCTAA CGTGTGTGTG TGTGTGAAG TAC ACT      702
                                                      Tyr Thr

GAT GAA GGC AAC TTT GTACGTCCCA CGCATGGTCC TCAATTCTCT TATCTGGCAG    757
Asp Glu Gly Asn Phe
165

CCATGTGGTC ATTGTCGACG TTGCTAACTT GCGTAG GAT ATC GTC GGA AAC AAC    811
                                        Asp Ile Val Gly Asn Asn
                                            170             175

ATC CCG GTA TTC TTC ATT CAA GAT GCA ATC CAG TTC CCT GAC CTT ATC    859
Ile Pro Val Phe Phe Ile Gln Asp Ala Ile Gln Phe Pro Asp Leu Ile
            180                 185                 190

CAC TCG GTC AAG CCG CGT CCC GAC AAC GAG ATT CCC CAA GCG GCG ACG    907
His Ser Val Lys Pro Arg Pro Asp Asn Glu Ile Pro Gln Ala Ala Thr
                195                 200                 205

GCT CAT GAT TCA GCT TGG GAC TTC TTC AGC CAG CAG CCA AGC ACC ATG    955
Ala His Asp Ser Ala Trp Asp Phe Phe Ser Gln Gln Pro Ser Thr Met
            210                 215                 220

GTAAGCAATG GACCAAGGAG CCGCACCTGG GGTGACATGC CAGGGAGTAC ACAAGGCGTT  1015
CCGATGACCC TCGTGTGACC AAGGCAGTAC AACACTCCAC GGAGGACTCG AAGAGATTCG  1075
GCAATATGGA ACACAGAACT GACAGGATGG TAG CAC ACG TTG TTC TGG GCC ATG   1129
                                    His Thr Leu Phe Trp Ala Met
                                    225                 230

TCC GGC CAC GGA ATC CCT CGC AGC TAC CGC CAT ATG GTACGTTTGC         1175
Ser Gly His Gly Ile Pro Arg Ser Tyr Arg His Met
            235                 240

CTGGCTGAGA TGACCGTGAA TCCATTTCTA ACCTCAAGCC CAG GAT GGC TTC GGC    1230
                                                Asp Gly Phe Gly
                                                            245

GTC CAC ACG TTC CGG TTT GTC AAA GAT GAC GGC TCG TCC AAG TTG ATC    1278
Val His Thr Phe Arg Phe Val Lys Asp Asp Gly Ser Ser Lys Leu Ile
            250                 255                 260

AAG TGG CAT TTC AAG TCA CGC CAG GGA AAG GCG AGT CTA GTC TGG GAA    1326
Lys Trp His Phe Lys Ser Arg Gln Gly Lys Ala Ser Leu Val Trp Glu
        265                 270                 275

GAG GCG CAG GTT CTT TCT GGC AAG AAT GCC GAC TTC CAC CGT CAG GAC    1374
Glu Ala Gln Val Leu Ser Gly Lys Asn Ala Asp Phe His Arg Gln Asp
280                 285                 290

CTC TGG GAT GCT ATT GAG TCC GGG AAC GGA CCA GAA TGG GAT GTC TGC    1422
Leu Trp Asp Ala Ile Glu Ser Gly Asn Gly Pro Glu Trp Asp Val Cys
295             300                 305                 310

GTC CAG ATT GTC GAT GAG TCC CAG GCG CAA GCC TTT GGC TTC GAC TTG    1470
Val Gln Ile Val Asp Glu Ser Gln Ala Gln Ala Phe Gly Phe Asp Leu
            315                 320                 325

CTG GAC CCG ACA AAG ATC ATC CCC GAG GAG TAC GCC CCC TTG ACG AAG    1518
Leu Asp Pro Thr Lys Ile Ile Pro Glu Glu Tyr Ala Pro Leu Thr Lys
```

-continued

| | | | | | | | | | | | | | | | | |
|---|---|---|---|---|---|---|---|---|---|---|---|---|---|---|---|---|
| | | | | 330 | | | | | 335 | | | | | 340 | | |
| CTG | GGC | CTC | TTG | AAG | CTG | GAT | CGC | AAT | CCG | ACC | AAC | TAC | TTC | GCC | GAG | 1566 |
| Leu | Gly | Leu | Leu | Lys | Leu | Asp | Arg | Asn | Pro | Thr | Asn | Tyr | Phe | Ala | Glu | |
| | | 345 | | | | | 350 | | | | | 355 | | | | |
| ACG | GAG | CAG | GTC | ATG | TTC | CAA | CCC | GGT | CAT | ATC | GTC | CGC | GGC | ATC | GAC | 1614 |
| Thr | Glu | Gln | Val | Met | Phe | Gln | Pro | Gly | His | Ile | Val | Arg | Gly | Ile | Asp | |
| 360 | | | | | 365 | | | | | 370 | | | | | | |
| TTC | ACG | GAG | GAT | CCC | CTG | CTA | CAG | GGA | CGC | CTC | TTT | TCG | TAC | CTT | GAC | 1662 |
| Phe | Thr | Glu | Asp | Pro | Leu | Leu | Gln | Gly | Arg | Leu | Phe | Ser | Tyr | Leu | Asp | |
| 375 | | | | | 380 | | | | | 385 | | | | | 390 | |
| ACG | CAG | CTG | AAC | CGG | AAT | GGC | GGG | CCC | AAC | TTT | GAG | CAG | CTG | CCC | ATC | 1710 |
| Thr | Gln | Leu | Asn | Arg | Asn | Gly | Gly | Pro | Asn | Phe | Glu | Gln | Leu | Pro | Ile | |
| | | | | 395 | | | | | 400 | | | | | 405 | | |
| AAC | ATG | CCG | CGG | GTG | CCG | ATT | CAC | AAC | AAT | AAT | CGC | GAC | GGC | GCC | GGC | 1758 |
| Asn | Met | Pro | Arg | Val | Pro | Ile | His | Asn | Asn | Asn | Arg | Asp | Gly | Ala | Gly | |
| | | | 410 | | | | | 415 | | | | | 420 | | | |
| CAG | ATG | TTC | ATC | CAC | AGG | AAC | AAG | TAT | CCT | GTAAGTGCCT | | CTTTTGCCTC | | | | 1808 |
| Gln | Met | Phe | Ile | His | Arg | Asn | Lys | Tyr | Pro | | | | | | | |
| | | | 425 | | | | | 430 | | | | | | | | |
| GATCGTTGTG | | GTGCCGGCTT | | GCTGACAGAC | | GCAG | TAC | ACT | CCC | AAC | ACC | CTG | | | | 1860 |
| | | | | | | | Tyr | Thr | Pro | Asn | Thr | Leu | | | | |
| | | | | | | | | | | | | 435 | | | | |
| AAC | AGT | GGT | TAT | CCG | CGG | CAA | GCC | AAC | CAA | AAT | GCC | GGA | CGC | GGA | TTC | 1908 |
| Asn | Ser | Gly | Tyr | Pro | Arg | Gln | Ala | Asn | Gln | Asn | Ala | Gly | Arg | Gly | Phe | |
| | | 440 | | | | | 445 | | | | | 450 | | | | |
| TTC | ACA | GCG | CCT | GGC | CGT | ACC | GCC | AGC | GGT | GCC | CTC | GTC | CGT | GAG | GTG | 1956 |
| Phe | Thr | Ala | Pro | Gly | Arg | Thr | Ala | Ser | Gly | Ala | Leu | Val | Arg | Glu | Val | |
| 455 | | | | | 460 | | | | | 465 | | | | | 470 | |
| TCG | CCA | ACA | TTC | AAC | GAC | CAC | TGG | TCG | CAG | CCC | CGT | CTC | TTC | TTC | AAC | 2004 |
| Ser | Pro | Thr | Phe | Asn | Asp | His | Trp | Ser | Gln | Pro | Arg | Leu | Phe | Phe | Asn | |
| | | | | 475 | | | | | 480 | | | | | 485 | | |
| TCC | CTC | ACT | CCC | GTC | GAA | CAA | CAG | TTC | CTC | GTC | AAC | GCC | ATG | CGC | TTC | 2052 |
| Ser | Leu | Thr | Pro | Val | Glu | Gln | Gln | Phe | Leu | Val | Asn | Ala | Met | Arg | Phe | |
| | | | 490 | | | | | 495 | | | | | 500 | | | |
| GAA | ATC | AGC | CTT | GTG | AAG | TCG | GAA | GAA | GTC | AAG | AAG | AAC | GTG | CTC | ACC | 2100 |
| Glu | Ile | Ser | Leu | Val | Lys | Ser | Glu | Glu | Val | Lys | Lys | Asn | Val | Leu | Thr | |
| | | 505 | | | | | 510 | | | | | 515 | | | | |
| CAG | CTC | AAC | CGC | GTC | AGC | CAT | GAC | GTG | GCC | GTG | CGC | GTG | GCC | GCC | GCT | 2148 |
| Gln | Leu | Asn | Arg | Val | Ser | His | Asp | Val | Ala | Val | Arg | Val | Ala | Ala | Ala | |
| 520 | | | | | 525 | | | | | 530 | | | | | | |
| ATC | GGC | CTC | GGC | GCG | CCC | GAC | GCG | GAC | GAC | ACA | TAC | TAC | CAC | AAC | AAC | 2196 |
| Ile | Gly | Leu | Gly | Ala | Pro | Asp | Ala | Asp | Asp | Thr | Tyr | Tyr | His | Asn | Asn | |
| 535 | | | | | 540 | | | | | 545 | | | | | 550 | |
| AAG | ACG | GCT | GGC | GTC | TCA | ATC | GTT | GGA | AGC | GGG | CCC | TTG | CCT | ACC | ATC | 2244 |
| Lys | Thr | Ala | Gly | Val | Ser | Ile | Val | Gly | Ser | Gly | Pro | Leu | Pro | Thr | Ile | |
| | | | | 555 | | | | | 560 | | | | | 565 | | |
| AAG | ACT | CTC | CGC | GTC | GGC | ATC | CTG | GCT | ACC | ACG | AGC | GAG | TCG | AGC | GCG | 2292 |
| Lys | Thr | Leu | Arg | Val | Gly | Ile | Leu | Ala | Thr | Thr | Ser | Glu | Ser | Ser | Ala | |
| | | | 570 | | | | | 575 | | | | | 580 | | | |
| CTG | GAT | CAG | GCG | GCC | CAG | CTC | CGC | ACC | CGT | CTG | GAA | AAG | GAC | GGG | CTT | 2340 |
| Leu | Asp | Gln | Ala | Ala | Gln | Leu | Arg | Thr | Arg | Leu | Glu | Lys | Asp | Gly | Leu | |
| | | 585 | | | | | 590 | | | | | 595 | | | | |
| GTG | GTC | ACG | GTT | GTG | GCT | GAA | ACG | CTG | CGC | GAG | GGG | GTA | GAC | CAG | ACG | 2388 |
| Val | Val | Thr | Val | Val | Ala | Glu | Thr | Leu | Arg | Glu | Gly | Val | Asp | Gln | Thr | |
| | | 600 | | | | | 605 | | | | | 610 | | | | |
| TAC | TCG | ACG | GCG | GAT | GCC | ACG | GGT | TTC | GAC | GGC | GTT | GTT | GTG | GAC | 2436 |
| Tyr | Ser | Thr | Ala | Asp | Ala | Thr | Gly | Phe | Asp | Gly | Val | Val | Val | Asp | |
| 615 | | | | | 620 | | | | | 625 | | | | | 630 | |
| GGG | GCG | GCG | GCG | CTG | TTT | GCC | AGC | ACC | GCG | TCG | TCG | CCG | TTG | TTC | CCG | 2484 |
| Gly | Ala | Ala | Ala | Leu | Phe | Ala | Ser | Thr | Ala | Ser | Ser | Pro | Leu | Phe | Pro | |

|   |   |   |   |   | 635 |   |   |   |   | 640 |   |   |   |   | 645 |   |   |   |      |
|---|---|---|---|---|---|---|---|---|---|---|---|---|---|---|---|---|---|---|------|
| ACG | GGC | AGG | CCG | TTG | CAG | ATC | TTT | GTG | GAC | GCG | TAT | CGG | TGG | GGA | AAG | | | | 2532 |
| Thr | Gly | Arg | Pro | Leu | Gln | Ile | Phe | Val | Asp | Ala | Tyr | Arg | Trp | Gly | Lys | | | | |
| | | | 650 | | | | | 655 | | | | | 660 | | | | | | |

| CCG | GTC | GGT | GTG | TGT | GGT | GGG | AAG | TCG | AGC | GAG | GTG | TTG | GAT | GCG | GCG | 2580 |
|---|---|---|---|---|---|---|---|---|---|---|---|---|---|---|---|---|
| Pro | Val | Gly | Val | Cys | Gly | Gly | Lys | Ser | Ser | Glu | Val | Leu | Asp | Ala | Ala | |
| | | 665 | | | | 670 | | | | | 675 | | | | | |

| GAT | GTT | CCG | GAA | GAC | GGG | GAC | GGG | GTG | TAT | TCG | GAG | GAG | TCG | GTG | GAC | 2628 |
|---|---|---|---|---|---|---|---|---|---|---|---|---|---|---|---|---|
| Asp | Val | Pro | Glu | Asp | Gly | Asp | Gly | Val | Tyr | Ser | Glu | Glu | Ser | Val | Asp | |
| | 680 | | | | 685 | | | | | 690 | | | | | | |

| ATG | TTT | GTG | GAG | GAG | TTT | GAG | AAG | GGG | TTG | GCT | ACT | TTC | AGG | 2670 |
|---|---|---|---|---|---|---|---|---|---|---|---|---|---|---|
| Met | Phe | Val | Glu | Glu | Phe | Glu | Lys | Gly | Leu | Ala | Thr | Phe | Arg | |
| 695 | | | | 700 | | | | | 705 | | | | | |

GTGAGTCTTG ATGCCTTTGT TTGTTGTGAT GTTATTGTTT TGTTTTGTCT CGGACTTTGT 2730

| GAAAGAATGA | CGGACTGACG | TCTTTGGTAT | CTAG | TTT | ACC | GAT | CGG | TTT | GCT | 2782 |
|---|---|---|---|---|---|---|---|---|---|---|
| | | | | Phe | Thr | Asp | Arg | Phe | Ala | |
| | | | | | | 710 | | | | |

| CTC | GAC | TCT | TAG | 2794 |
|---|---|---|---|---|
| Leu | Asp | Ser | | |
| 715 | | | | |

( 2 ) INFORMATION FOR SEQ ID NO:2:

( i ) SEQUENCE CHARACTERISTICS:
        ( A ) LENGTH: 717 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asn | Arg | Val | Thr | Asn | Leu | Leu | Ala | Trp | Ala | Gly | Ala | Ile | Gly | Leu |
|---|---|---|---|---|---|---|---|---|---|---|---|---|---|---|---|
| 1 | | | | 5 | | | | | 10 | | | | | 15 | |

| Ala | Gln | Ala | Thr | Cys | Pro | Phe | Ala | Asp | Pro | Ala | Ala | Leu | Tyr | Ser | Arg |
|---|---|---|---|---|---|---|---|---|---|---|---|---|---|---|---|
| | | | 20 | | | | | 25 | | | | | 30 | | |

| Gln | Asp | Thr | Thr | Ser | Gly | Gln | Ser | Pro | Leu | Ala | Ala | Tyr | Glu | Val | Asp |
|---|---|---|---|---|---|---|---|---|---|---|---|---|---|---|---|
| | | | 35 | | | | 40 | | | | | 45 | | | |

| Asp | Ser | Thr | Gly | Tyr | Leu | Thr | Ser | Asp | Val | Gly | Gly | Pro | Ile | Gln | Asp |
|---|---|---|---|---|---|---|---|---|---|---|---|---|---|---|---|
| | 50 | | | | | 55 | | | | | 60 | | | | |

| Gln | Thr | Ser | Leu | Lys | Ala | Gly | Ile | Arg | Gly | Pro | Thr | Leu | Leu | Glu | Asp |
|---|---|---|---|---|---|---|---|---|---|---|---|---|---|---|---|
| 65 | | | | | 70 | | | | | 75 | | | | | 80 |

| Phe | Met | Phe | Arg | Gln | Lys | Ile | Gln | His | Phe | Asp | His | Glu | Arg | Val | Pro |
|---|---|---|---|---|---|---|---|---|---|---|---|---|---|---|---|
| | | | | 85 | | | | | 90 | | | | | 95 | |

| Glu | Arg | Ala | Val | His | Ala | Arg | Gly | Ala | Gly | Ala | His | Gly | Thr | Phe | Thr |
|---|---|---|---|---|---|---|---|---|---|---|---|---|---|---|---|
| | | | 100 | | | | | 105 | | | | | 110 | | |

| Ser | Tyr | Ala | Asp | Trp | Ser | Asn | Ile | Thr | Ala | Ala | Ser | Phe | Leu | Asn | Ala |
|---|---|---|---|---|---|---|---|---|---|---|---|---|---|---|---|
| | | | 115 | | | | | 120 | | | | | 125 | | |

| Thr | Gly | Lys | Gln | Thr | Pro | Val | Phe | Val | Arg | Phe | Ser | Thr | Val | Ala | Gly |
|---|---|---|---|---|---|---|---|---|---|---|---|---|---|---|---|
| | | | 130 | | | | | 135 | | | | 140 | | | |

| Ser | Arg | Gly | Ser | Ala | Asp | Thr | Ala | Arg | Asp | Val | His | Gly | Phe | Ala | Thr |
|---|---|---|---|---|---|---|---|---|---|---|---|---|---|---|---|
| 145 | | | | | 150 | | | | | 155 | | | | | 160 |

| Arg | Phe | Tyr | Thr | Asp | Glu | Gly | Asn | Phe | Asp | Ile | Val | Gly | Asn | Asn | Ile |
|---|---|---|---|---|---|---|---|---|---|---|---|---|---|---|---|
| | | | | 165 | | | | | 170 | | | | | 175 | |

| Pro | Val | Phe | Phe | Ile | Gln | Asp | Ala | Ile | Gln | Phe | Pro | Asp | Leu | Ile | His |
|---|---|---|---|---|---|---|---|---|---|---|---|---|---|---|---|
| | | | | 180 | | | | | 185 | | | | | 190 | |

| Ser | Val | Lys | Pro | Arg | Pro | Asp | Asn | Glu | Ile | Pro | Gln | Ala | Ala | Thr | Ala |
|---|---|---|---|---|---|---|---|---|---|---|---|---|---|---|---|
| | | | 195 | | | | | 200 | | | | | 205 | | |

| His | Asp | Ser | Ala | Trp | Asp | Phe | Phe | Ser | Gln | Gln | Pro | Ser | Thr | Met | His |
|---|---|---|---|---|---|---|---|---|---|---|---|---|---|---|---|

-continued

|  |  |  |  |  | 210 |  |  |  |  | 215 |  |  |  |  | 220 |  |  |
|---|---|---|---|---|---|---|---|---|---|---|---|---|---|---|---|---|---|
| Thr | Leu | Phe | Trp | Ala | Met | Ser | Gly | His | Gly | Ile | Pro | Arg | Ser | Tyr | Arg |
| 225 |  |  |  |  | 230 |  |  |  |  | 235 |  |  |  |  | 240 |
| His | Met | Asp | Gly | Phe | Gly | Val | His | Thr | Phe | Arg | Phe | Val | Lys | Asp | Asp |
|  |  |  | 245 |  |  |  |  | 250 |  |  |  |  | 255 |  |  |
| Gly | Ser | Ser | Lys | Leu | Ile | Lys | Trp | His | Phe | Lys | Ser | Arg | Gln | Gly | Lys |
|  |  |  | 260 |  |  |  |  | 265 |  |  |  |  | 270 |  |  |
| Ala | Ser | Leu | Val | Trp | Glu | Glu | Ala | Gln | Val | Leu | Ser | Gly | Lys | Asn | Ala |
|  |  | 275 |  |  |  |  | 280 |  |  |  |  | 285 |  |  |  |
| Asp | Phe | His | Arg | Gln | Asp | Leu | Trp | Asp | Ala | Ile | Glu | Ser | Gly | Asn | Gly |
|  | 290 |  |  |  |  | 295 |  |  |  |  | 300 |  |  |  |  |
| Pro | Glu | Trp | Asp | Val | Cys | Val | Gln | Ile | Val | Asp | Glu | Ser | Gln | Ala | Gln |
| 305 |  |  |  |  | 310 |  |  |  |  | 315 |  |  |  |  | 320 |
| Ala | Phe | Gly | Phe | Asp | Leu | Leu | Asp | Pro | Thr | Lys | Ile | Ile | Pro | Glu | Glu |
|  |  |  |  | 325 |  |  |  |  | 330 |  |  |  |  | 335 |  |
| Tyr | Ala | Pro | Leu | Thr | Lys | Leu | Gly | Leu | Leu | Lys | Leu | Asp | Arg | Asn | Pro |
|  |  |  | 340 |  |  |  |  | 345 |  |  |  |  | 350 |  |  |
| Thr | Asn | Tyr | Phe | Ala | Glu | Thr | Glu | Gln | Val | Met | Phe | Gln | Pro | Gly | His |
|  |  | 355 |  |  |  |  | 360 |  |  |  |  | 365 |  |  |  |
| Ile | Val | Arg | Gly | Ile | Asp | Phe | Thr | Glu | Asp | Pro | Leu | Leu | Gln | Gly | Arg |
|  | 370 |  |  |  |  | 375 |  |  |  |  | 380 |  |  |  |  |
| Leu | Phe | Ser | Tyr | Leu | Asp | Thr | Gln | Leu | Asn | Arg | Asn | Gly | Gly | Pro | Asn |
| 385 |  |  |  |  | 390 |  |  |  |  | 395 |  |  |  |  | 400 |
| Phe | Glu | Gln | Leu | Pro | Ile | Asn | Met | Pro | Arg | Val | Pro | Ile | His | Asn | Asn |
|  |  |  |  | 405 |  |  |  |  | 410 |  |  |  |  | 415 |  |
| Asn | Arg | Asp | Gly | Ala | Gly | Gln | Met | Phe | Ile | His | Arg | Asn | Lys | Tyr | Pro |
|  |  |  | 420 |  |  |  |  | 425 |  |  |  |  | 430 |  |  |
| Tyr | Thr | Pro | Asn | Thr | Leu | Asn | Ser | Gly | Tyr | Pro | Arg | Gln | Ala | Asn | Gln |
|  |  | 435 |  |  |  |  | 440 |  |  |  |  | 445 |  |  |  |
| Asn | Ala | Gly | Arg | Gly | Phe | Phe | Thr | Ala | Pro | Gly | Arg | Thr | Ala | Ser | Gly |
|  | 450 |  |  |  |  | 455 |  |  |  |  | 460 |  |  |  |  |
| Ala | Leu | Val | Arg | Glu | Val | Ser | Pro | Thr | Phe | Asn | Asp | His | Trp | Ser | Gln |
| 465 |  |  |  |  | 470 |  |  |  |  | 475 |  |  |  |  | 480 |
| Pro | Arg | Leu | Phe | Phe | Asn | Ser | Leu | Thr | Pro | Val | Glu | Gln | Gln | Phe | Leu |
|  |  |  |  | 485 |  |  |  |  | 490 |  |  |  |  | 495 |  |
| Val | Asn | Ala | Met | Arg | Phe | Glu | Ile | Ser | Leu | Val | Lys | Ser | Glu | Glu | Val |
|  |  |  | 500 |  |  |  |  | 505 |  |  |  |  | 510 |  |  |
| Lys | Lys | Asn | Val | Leu | Thr | Gln | Leu | Asn | Arg | Val | Ser | His | Asp | Val | Ala |
|  |  | 515 |  |  |  |  | 520 |  |  |  |  | 525 |  |  |  |
| Val | Arg | Val | Ala | Ala | Ala | Ile | Gly | Leu | Gly | Ala | Pro | Asp | Ala | Asp | Asp |
|  | 530 |  |  |  |  | 535 |  |  |  |  | 540 |  |  |  |  |
| Thr | Tyr | Tyr | His | Asn | Asn | Lys | Thr | Ala | Gly | Val | Ser | Ile | Val | Gly | Ser |
| 545 |  |  |  |  | 550 |  |  |  |  | 555 |  |  |  |  | 560 |
| Gly | Pro | Leu | Pro | Thr | Ile | Lys | Thr | Leu | Arg | Val | Gly | Ile | Leu | Ala | Thr |
|  |  |  |  | 565 |  |  |  |  | 570 |  |  |  |  | 575 |  |
| Thr | Ser | Glu | Ser | Ser | Ala | Leu | Asp | Gln | Ala | Ala | Gln | Leu | Arg | Thr | Arg |
|  |  |  | 580 |  |  |  |  | 585 |  |  |  |  | 590 |  |  |
| Leu | Glu | Lys | Asp | Gly | Leu | Val | Thr | Val | Val | Ala | Glu | Thr | Leu | Arg |
|  |  | 595 |  |  |  |  | 600 |  |  |  |  | 605 |  |  |  |
| Glu | Gly | Val | Asp | Gln | Thr | Tyr | Ser | Thr | Ala | Asp | Ala | Thr | Gly | Phe | Asp |
|  | 610 |  |  |  |  | 615 |  |  |  |  | 620 |  |  |  |  |
| Gly | Val | Val | Val | Val | Asp | Gly | Ala | Ala | Ala | Leu | Phe | Ala | Ser | Thr | Ala |
| 625 |  |  |  |  | 630 |  |  |  |  | 635 |  |  |  |  | 640 |

| Ser | Ser | Pro | Leu | Phe 645 | Pro | Thr | Gly | Arg | Pro 650 | Leu | Gln | Ile | Phe | Val 655 | Asp |

| Ala | Tyr | Arg | Trp 660 | Gly | Lys | Pro | Val | Gly 665 | Val | Cys | Gly | Gly | Lys 670 | Ser | Ser |

| Glu | Val | Leu 675 | Asp | Ala | Ala | Asp | Val 680 | Pro | Glu | Asp | Gly | Asp 685 | Gly | Val | Tyr |

| Ser | Glu 690 | Glu | Ser | Val | Asp | Met 695 | Phe | Val | Glu | Glu | Phe 700 | Glu | Lys | Gly | Leu |

| Ala 705 | Thr | Phe | Arg | Phe | Thr 710 | Asp | Arg | Phe | Ala | Leu 715 | Asp | Ser |

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: N=deoxyinosine
        (B) LOCATION: 24

(xi) SEQUENCE DESCRIPTION: SEQ ID NO:3:

AGCACTAGTT TAAACTA Y GA RGTNGA Y GA    29

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:4:

TATTGGATAT AAGCGGCCGC CC Y T-
GNCG Y T T Y TTGAARTG    40

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

CCGCGGCGTC CTTTCTGA    18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

GATCTTTGTC GGGTCCAG    18

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear ( x i ) SEQUENCE DESCRIPTION: SEQ ID NO:7:

```
Ser  Gly  Gln  Ser  Pro  Leu  Ala  Ala  Tyr  Glu  Val  Asp  Asp  Ser  Asp  Gly
1                 5                             10                            15

Tyr
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Ser  Gly  Gln  Ser  Pro  Leu  Ala  Ala  Tyr  Glu  Val  Asp  Asp  Ser  Thr  Gly
1                 5                             10                            15

Tyr
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Ala  Asp  Trp  Ser  Ile  Thr  Ala  Ala
1                 5
```

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Ala  Asp  Trp  Ser  Asn  Ile  Thr  Ala  Ala
1                 5
```

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

```
Arg  Asn  Pro  Thr  Asn  Tyr  Phe  Ala  Glu
1                 5
```

( 2 ) INFORMATION FOR SEQ ID NO:12:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Ala  Tyr  Arg  Trp  Gly  Lys  Pro  Val  Gly  Val  Xaa  Gly  Gly  Lys  Arg  Arg
1                 5                             10                            15
```

Glu ( 2 ) INFORMATION FOR SEQ ID NO:13:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

```
Ala Tyr Arg Trp Gly Lys Pro Val Gly Val Cys Gly Gly Lys Ser Ser
 1               5                  10                  15
Glu
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
Ser Phe Ala Leu Asp Gln Ala Ala Gln Leu Arg
 1               5                  10
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
Arg Phe Glu Ile Ser Leu Val Lys
 1               5
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
Asn Val Leu Thr Gln Leu Asn Arg Val
 1               5
```

( 2 ) INFORMATION FOR SEQ ID NO:17:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

```
Met Asp Gly Phe Gly Val His Thr Phe Arg Phe Val Lys Asp Asp Gly
 1               5                  10                  15
Ser Ser Lys Leu Ile Lys Xaa His Phe Lys Lys Arg Gln Gly Lys Ala
                20              25                  30
```

( 2 ) INFORMATION FOR SEQ ID NO:18:

(i) SEQUENCE CHARACTERISTICS:
    (A) LENGTH: 32 amino acids
    (B) TYPE: amino acid
    (C) STRANDEDNESS: single
    (D) TOPOLOGY: linear (xi) SEQUENCE DESCRIPTION: SEQ ID NO:18:

```
Met Asp Gly Phe Gly Val His Thr Phe Arg Phe Val Lys Asp Asp Gly
 1               5                  10                  15

Ser Ser Lys Leu Ile Lys Trp His Phe Lys Ser Arg Gln Gly Lys Ala
             20                  25                  30
```